(12) United States Patent
Lobovsky et al.

(10) Patent No.: US 6,753,082 B1
(45) Date of Patent: Jun. 22, 2004

(54) ABSORBENT FIBERS

(75) Inventors: Alexander Lobovsky, New Providence, NJ (US); James Matrunich, Mountainside, NJ (US); John B. Boyle, Chester, VA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/374,626

(22) Filed: Feb. 26, 2003

(51) Int. Cl.$^7$ ................................................. D01F 6/00
(52) U.S. Cl. ...................... 428/397; 428/399; 428/362; 428/401
(58) Field of Search ................................ 428/362, 397, 428/399, 401

(56) References Cited

U.S. PATENT DOCUMENTS

| | | | |
|---|---|---|---|
| 4,707,409 A | 11/1987 | Phillips | 428/397 |
| 5,057,368 A | 10/1991 | Largman et al. | 428/397 |
| 5,124,205 A | 6/1992 | Raynolds et al. | 428/364 |
| 5,200,248 A | 4/1993 | Thopson et al. | 428/131 |
| 5,268,229 A | 12/1993 | Phillips et al. | 428/400 |
| 5,496,627 A | 3/1996 | Bagrodia et al. | 428/284 |
| 5,972,505 A | 10/1999 | Phillips et al. | 428/397 |
| 5,977,429 A | 11/1999 | Phillips et al. | 604/370 |
| 6,093,491 A | 7/2000 | Dugan et al. | 428/397 |
| 6,296,821 B1 | 10/2001 | Hendricks et al. | 423/237 |

FOREIGN PATENT DOCUMENTS

WO WO98/07909 2/1998 .......... D01D/5/253

Primary Examiner—N. Edwards

(57) ABSTRACT

Novel fibers having improved liquid absorption capacity combined with the ability to provide a dry feeling even when nearly saturated. The fibers are expected to be useful in diverse applications such as diapers, incontinent briefs, feminine hygiene napkins, tampons, surgical sponges, wound dressings, towels, separation of oil from the surface of water, and the containment or collection of oil in industrial installations.

24 Claims, 9 Drawing Sheets

ABSORBENT FIBERS

BACKGROUND OF THE INVENTION

1. Field of the Invention

This invention relates to fibers having improved liquid absorption capacity combined with the ability to provide a dry feeling even when nearly saturated.

2. Description of the Related Art

Articles having liquid absorption capabilities have found diverse applications in areas such as diapers, incontinent briefs, feminine hygiene napkins, tampons, surgical sponges, wound dressings, towels, separation of oil from the surface of water, and the containment or collection of oil in industrial installations. Generally, the utility of such articles is based on fibers having suitable absorbent structures.

Absorbent fibers have been described for example in U.S. Pat. Nos. 4,707,409; 5,057,368; 5,124,205; 5,200,248; 5,268,229; 5,496,627; 5,972,505; 5,977,429; 6,093,491; 6,296,821B1 and in WO 98/07909. U.S. Pat. No. 4,707,409 describes a filament with a four-winged cross-section. U.S. Pat. No. 5,057,368 describes multilobal fibers wherein each lobe has a leg and a cap. U.S. Pat. No. 5,124,205 describes a grooved filament wherein the surface roughness at the bottom of a groove is greater than outside of the groove. The surface roughness is produced by a chemical etching technique. U.S. Pat. No. 5,200,248 describes capillary channel structures having a "Specific Capillary Volume" of at least about 2.0 cc/g and a "Specific Capillary Surface Areas" of at least about 2000 cm$^2$/g. U.S. Pat. No. 5,268,229 describes filaments having "U" and "E" shaped cross-sections with stabilizing legs. U.S. Pat. No. 5,496,627 describes filaments having a "cross-sectional shape factor" greater than 1.5 and a specific volume of about 1.5–5 cc/g. U.S. Pat. No. 5,972,505 describes fibers having arms extending from both sides of a central spine. U.S.P. describes fibers 2 to 37 mm in length and having varying cross-sectional shapes along their length. U.S. Pat. No. 6,093,491 describes grooved filaments where the cross-sectional area of the groove is greater than or equal to $\pi/8$ times the square of the width of the groove mouth. WO 98/07909 describes a bundle of synthetic fibers wherein the filaments comprising the bundle have a "Single Fiber Bulk Factor" greater than 4.0, the bundle has a "Specific Volume" greater than 4.0 cc/g and certain "Maximum Potential Flux" values.

Each of the fibers cited above represented progress toward the goals to which they were directed. However, none described the specific constructions of the present invention and none satisfied the needs met by this invention. A need exists for fibers that have high liquid absorption capacity combined with the ability to provide a dry feeling even when nearly saturated.

SUMMARY OF THE INVENTION

The invention provides novel fibers for use in applications such as diapers, incontinent briefs, feminine hygiene napkins, tampons, surgical sponges, wound dressings and towels and in applications such as flotation booms suitable for the containment and collection of oil from the surface of water, and filters for the collection of oil from aqueous liquids.

The fibers of the invention having improved liquid absorption capability are comprised of a plurality of filaments having one or more capillary channels. Each such capillary channel is formed by capillary channel walls, and has a channel-opening dimension. The filaments comprising the fibers of the invention satisfy the following equations:

$$0.1 \leq A_f/A_{fp} \leq 0.8 \qquad \text{Eq. 1}$$

$$0.1 \leq \Psi \leq 1 \qquad \text{Eq. 2}$$

$$1 \leq d \leq 80 \qquad \text{Eq. 3}$$

$$1.75\Psi - 0.83\, A_f/A_{fp} - 0.017\, d + 1.48 \geq 0 \qquad \text{Eq. 4}$$

wherein $A_f$ is the cross-sectional area occupied by the material comprising the filament;

$A_{fp}$ is the footprint area of the filament cross-section;

d is the denier of the filament;

$\Psi$ is the ratio of the square root of the sum of the cross-sectional areas of the channels in a filament to the sum of the channel opening dimensions as expressed by following equation;

$$\Psi = \frac{\sqrt{\sum_{i=1}^{N} Ac(i)}}{\sum_{i=1}^{N} L(i)} \qquad \text{Eq. 5}$$

wherein

Ac(i) is the cross-sectional area of the i$^{th}$ channel;

L(i) is the dimension of the opening of the i$^{th}$ channel;

N is the number of channels; and wherein the fiber has a liquid absorption capacity of at least about two volumes of liquid per volume of fiber.

DETAILED DESCRIPTION OF THE INVENTION

Figure 1:
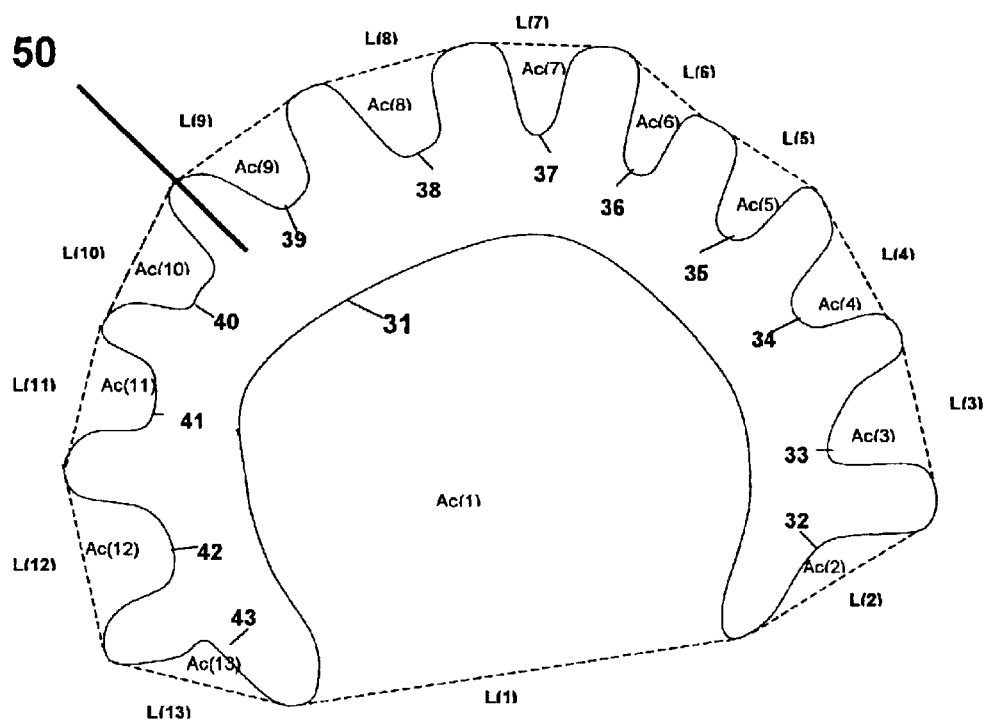
FIG. 1 shows a cross-sectional view of a corrugated U-shaped filament of a fiber of this invention, which exemplifies the measurements and procedure for determining the geometric characteristics of the filament.

The present invention provides novel fibers having improved liquid absorption capacity combined with the ability to provide a dry feeling even when nearly saturated. The fibers of the invention accomplish these results through the use of novel, specific geometries within narrow ranges. The fibers of the invention are assemblies of filaments (monofilaments). Where fiber cross-section is discussed below, it will be understood that reference is made to the filament cross-section unless otherwise stated.

The fibers of the invention provide two primary reservoirs for the sequestration of liquids. First, the filaments comprising the fibers possess one or more longitudinal capillary channels. Each such capillary channel is formed by capillary channel walls, and has a channel-opening dimension. The capillary channels provide one reservoir for the capture of liquids. The second significant reservoir for liquids is formed by the interfibrillar spaces in the fiber bundle.

It has been found that liquid absorption capacity is sensitively related to geometric parameters of the fibers. Among these parameters are:

the filament denier, grams/9000 meters the cross-sectional area occupied by the material comprising a filament in proportion to the footprint area of the filament cross-section, dimensionless the ratio of the square root of the sum of the cross-sectional areas of the channels in a filament to the sum of the channel opening dimensions, dimensionless.

Surprisingly, it has been found that the objectives of the invention are achieved when the relationships between these parameters satisfy the following equations:

$$0.1 \leq A_f/A_{fp} \leq 0.8 \qquad \text{Eq. 1}$$

$$0.1 \leq \Psi \leq 1 \qquad \text{Eq. 2}$$

$$1 \leq d \leq 80 \qquad \text{Eq. 3}$$

$$1.75\Psi - 0.83\, A_f/A_{fp} - 0.017\, d + 1.48 \geq 0 \qquad \text{Eq. 4}$$

wherein $A_f$ is the cross-sectional area occupied by the material comprising a filament;

$A_{fp}$ is the footprint area of the filament cross-section (see Equation 6);

d is the denier of the filament;

$\Psi$ is the ratio of the square root of the sum of the cross-sectional areas of the channels in a filament to the sum of the channel opening dimensions as expressed by following equation;

$$\Psi = \frac{\sqrt{\sum_{i=1}^{N} A_c(i)}}{\sum_{i=1}^{N} L(i)} \qquad \text{Eq. 5}$$

wherein $A_c(i)$ is the cross-sectional area of the $i^{th}$ channel;

$L(i)$ is the dimension of the opening of the $i^{th}$ channel; and

N is the number of channels.

The footprint area of a filament ($A_{fp}$) is the sum of the area occupied by the material of which the filament is constituted ($A_f$) and the areas of the capillary channels ($A_c(i)$) as expressed by the following equation:

$$A_{fp} = A_f + \sum_{i=1}^{N} A_c(i) \qquad \text{Eq. 6}$$

A fiber of the invention has a liquid absorption capacity of at least about two volumes of liquid per volume of fiber.

It will be understood that the fiber volume discussed herein throughout is the volume of the polymeric material constituting the fiber. It is equal to the fiber weight divided by the density of the polymer. The volumes of liquid and fiber are expressed in the same units, e.g., cc/cc.

Without being held to a particular theory of why the invention works with this selection of geometric parameters, it is believed that when the filament channel opening dimensions are either too large or too small in relation to the channel areas, liquids are either not held by the channels or cannot easily enter the channels. The shape of the filaments, as reflected in the cross-sectional area occupied by the material comprising a filament in proportion to the footprint area of the filament cross-section, affects the capacities of the inter-filament reservoirs, as does the filament denier. If the dimensions of the inter-filament reservoirs are too large or too small, the liquid is also not efficiently absorbed.

FIG. 1 shows a cross-sectional view of a corrugated U-shaped filament 50 of a fiber of this invention. FIG. 1 illustrates the measurements and procedure for determining the geometric characteristics of the filament. The filament 50 of FIG. 1 has one major capillary channel defined by capillary channel walls 31. Additionally, the filament has twelve minor capillary channels defined by capillary channel walls 32 to 43. The channel opening dimensions L(1) to L(13) are defined by straight line segments connecting the extremities of each capillary channel wall. The major capillary channel has a cross-sectional area Ac(1) and the minor capillary channels have cross-sectional areas Ac(2) to Ac(13). The footprint area of a filament is the sum of the area occupied by the material of which the filament is constituted and the areas of the capillary channels. For the filament illustrated in FIG. 1:

$$A_{fp} = A_f + A_c(1) + A_c(2) + A_c(3) + \ldots A_c(13)$$

The dimensions and areas of the filament cross-sections are conveniently measured by examining the filament cross-sections under a microscope and analyzing the image with appropriate software such as TCI Pro from Coreco Imaging Co., St. Lawrence, Canada.

Preferably, the filaments in a fiber of the invention satisfy the following relationship:

$$1.75\Psi - 0.83\, A_f/A_{fp} - 0.017\, d + 0.98 \geq 0 \qquad \text{Eq. 7}$$

More preferably, the filaments satisfy the following relationship:

$$1.75\Psi - 0.83\, A_f/A_{fp} - 0.017\, d + 0.48 \geq 0 \qquad \text{Eq. 8}$$

Most preferably, the filaments satisfy the relationship below:

$$1.75\Psi - 0.83\, A_f/A_{f_p} - 0.017\, d \geq 0 \qquad \text{Eq. 9}$$

It has been found that fibers comprised of filaments that satisfy Equation 8 will generally absorb more liquid than fibers comprised of filaments that satisfy Equation 7 but not Equation 8. Similarly, fibers comprised of filaments that satisfy Equation 9 will generally absorb more liquid than fibers comprised of filaments that satisfy Equation 8 but not Equation 9.

Preferably, the ratio of the cross-sectional area occupied by the material comprising a filament in proportion to the footprint area of the filament cross-section ($A_f/A_{f_p}$) is from about 0.2 to about 0.6.

Preferably, the ratio of the square root of the sum of the cross-sectional areas of the channels in a filament to the sum of the channel opening dimensions ($\Psi$) is from about 0.2 to about 0.8.

Preferably, the fiber has a liquid absorption capacity of at least about 2.5 volumes of liquid per volume of fiber. More preferably, the fiber has a liquid absorption capacity of at least about three volumes of liquid per volume of fiber. Most preferably, the fiber has a liquid absorption capacity of at least about 3.5 volumes of liquid per volume of fiber.

A fiber of the invention is comprised of about 10 to about 10,000 filaments. Preferably, the fiber is comprised of 50 to 2000 filaments. Preferably the filament denier is from about 3 to about 50. More preferably, the filament denier is from about 11 to about 50. Most preferably, the filament denier is from about 11 to 30.

A preferred fiber of the invention is comprised of about 50 to about 2,000 filaments, with each filament having one or more lengthwise capillary channels formed by capillary channel walls, and a channel opening dimension. Each filament satisfies the following equations:

$$0.2 \leq A_f/A_{f_p} \leq 0.6 \qquad \text{Eq. 10}$$

$$0.2 \leq \Psi \leq 0.8 \qquad \text{Eq. 11}$$

$$11 \leq d \leq 50 \qquad \text{Eq. 12}$$

$$2.75\Psi - 0.83\, A_f/A_{f_p} - 0.017\, d + 0.48 \geq 0 \qquad \text{Eq. 13}$$

wherein $A_f$ is the cross-sectional area occupied by the material comprising the filament;

$A_{f_p}$ is the footprint area of the filament cross-section as defined by Equation 6;

d is the denier of the filament;

$\Psi$ is the ratio of the square root of the sum of the cross-sectional areas of the channels in a filament to the sum of the channel opening dimensions as expressed by following equation;

$$\Psi = \frac{\sqrt{\sum_{i=1}^{N} Ac(i)}}{\sum_{i=1}^{N} L(i)} \qquad \text{Eq. 5}$$

wherein $Ac(i)$ is the cross-sectional area of the $i^{th}$ channel;

$L(i)$ is the dimension of the opening of the $i^{th}$ channel; and

N is the number of channels; and wherein said fiber has a liquid absorption capacity of at least about three volumes of liquid per volume of fiber.

The absorbent fibers of the invention are preferably formed from synthetic polymers by processes, such as melt spinning, wet spinning, dry spinning, gel spinning and others. Preferably, the fibers are melt spun. Preferably, the fibers are spun from multi-filament spinnerets in a continuous spin-draw process.

The polymer comprising the fibers is selected from the group consisting of polyamides, polyesters, polyolefins, polyacrylics, polyalcohols, polyethers, polyketones, polycarbonates, polysulfides, polyurethanes, cellulosics and polyvinyl derivatives. Polyolefins, polyesters and polyamides are preferred. Most preferred polymers are polypropylene, poly(ethylene terephthalate), poly(trimethylene terephthalate), nylon 6 and nylon 66.

Preferably, the fibers of the invention are additionally comprised of a hydrophilic polymer. Preferably, the hydrophilic polymer comprises less than about 5 wt. % of the fiber and is incorporated in the feed to the spinning process. Most preferably, the hydrophilic polymer is an acrylic acid modified polypropylene.

Liquid Absorption Measurement

Thin wall plastic tubing of 5.60 mm inside diameter is cut into sections of approximately 50.8 mm length. Each tubing section is weighed to a precision of 0.1 mg. A fiber whose absorption capacity is to be measured is threaded through a tubing section. This is accomplished by first pushing a 0.0076 cm diameter steel wire through the tubing, tying the wire to the fiber, pulling the fiber through the tubing and cutting off the fiber flush with the ends of the tubing. Several samples are prepared with different numbers of fibers. The tubing sections containing the fibers are weighed to determine the dry fiber weight and volume in each.

One end of a tubing section is vertically dipped 5 mm into a beaker of distilled water and held in position for 10 minutes. At the end of this time, the tubing section is removed from contact with the water and permitted to drain for one minute. Its external surface is dried and the tubing section is re-weighed to determine the weight and volume of liquid absorbed.

The percent of the tube volume occupied by liquid and fiber is calculated and recorded. The difference between 100% and the sum of liquid and fiber volume percentages corresponds to empty space in the tube.

EXAMPLE 1

A blend consisting of 99 wt. % nylon 6 (polycaprolactam) of formic acid viscosity (FAV) of 55, Grade MBM from Honeywell International Inc. and 1 wt. % acrylic acid modified polypropylene (POLYBOND® 1001 from Uniroyal Chemical) was fed into a capillary rheometer. In this, and in the following examples, FAV was determined by the method of ASTM D-789 using a solution of 11 grams of nylon 6 in 100 ml of 90% formic acid at 25° C.

The polymer was melted and extruded at 255° C. at the rate of about 1 g/min through a one-hole spinneret. The melt filament was cooled, solidified and taken up on a winder at 549 meters/min. The filament had the cross-sectional shape shown in FIG. 1.

Analysis of the filament cross-section yielded the following measurements where the terms are as previously defined:

$$A_f/A_{f_p} = 0.426 \quad \Psi = 0.20 \quad d = 17.4$$

These measurements satisfy the conditions expressed by Eq. 1 to Eq. 3.

Moreover, it is found that:

$$1.75\Psi - 0.83\, A_f/A_{fp} - 0.017\, d + 1.48 = 1.17$$

This satisfies the condition expressed by Eq. 4.

Figure 8:
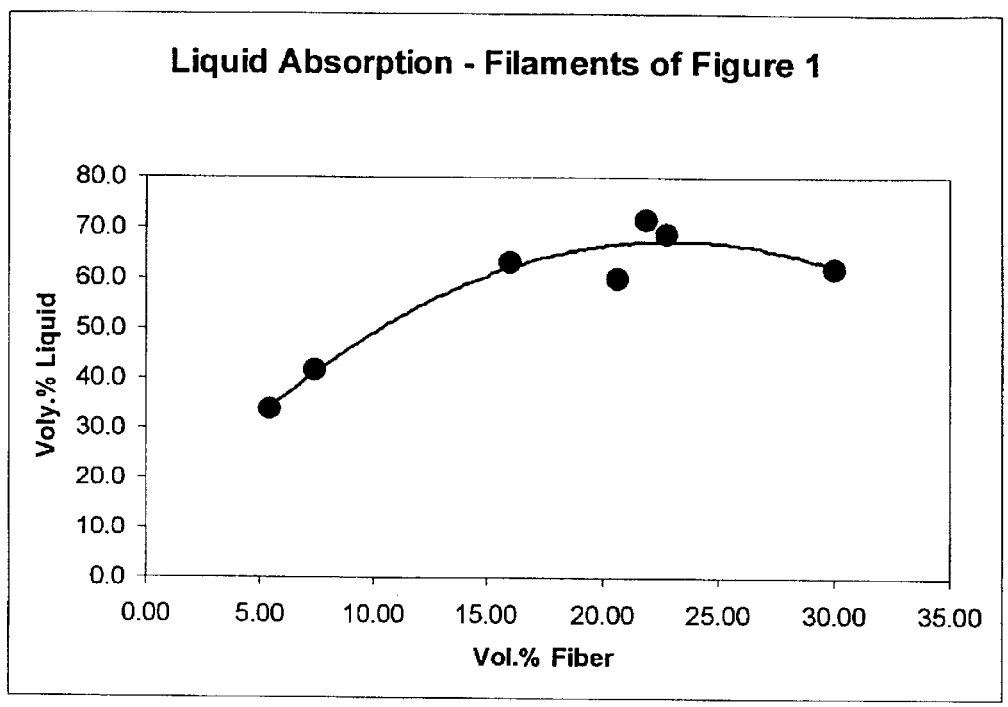
FIG. 8 shows a plot of liquid absorption vs. volume percent fiber for filaments having the cross-section illustrated in FIG. 1.

Filaments in a number from about 180 to about 1,010 were assembled into fibers and tested for absorbency by the method previously described yielding the data shown in FIG. 8. At the maximum in the absorption curve, 67 vol. % liquid was absorbed on 23 vol. % fiber corresponding to absorption of 2.91 volumes of liquid per volume of fiber.

Comparative Example

Figure 2:
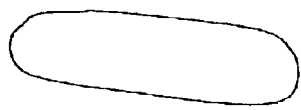
FIG. 2 shows a cross-section of an oval-shaped filament of a fiber not of this invention.

A blend consisting of 97 wt. % nylon 6 of formic acid viscosity (FAV) of 55, Grade MBM from Honeywell International Inc. and 3 wt. % acrylic acid modified polypropylene (POLYBOND® 1001) was fed into a capillary rheometer. The polymer was melted and extruded at 264° C. at the rate of about 4.8 g/min through a one-hole spinneret. The melt filament was cooled, solidified and taken up on a winder at 549 meters/min. The filament had the cross-sectional shape shown in FIG. 2.

Analysis of the filament cross-section yielded the following measurements where the terms are as previously defined:

$$A_f/A_{fp} = 0.953 \quad \Psi = 0.01 \quad d = 68.7$$

These measurements satisfy Equation 3 but not Equation 1 or Equation 2.
Moreover, it is found that:

$$1.75\Psi - 0.83\, A_f/A_{fp} - 0.017\, d + 1.48 = -0.46$$

This does not satisfy the condition expressed by Equation 4.

Figure 9:
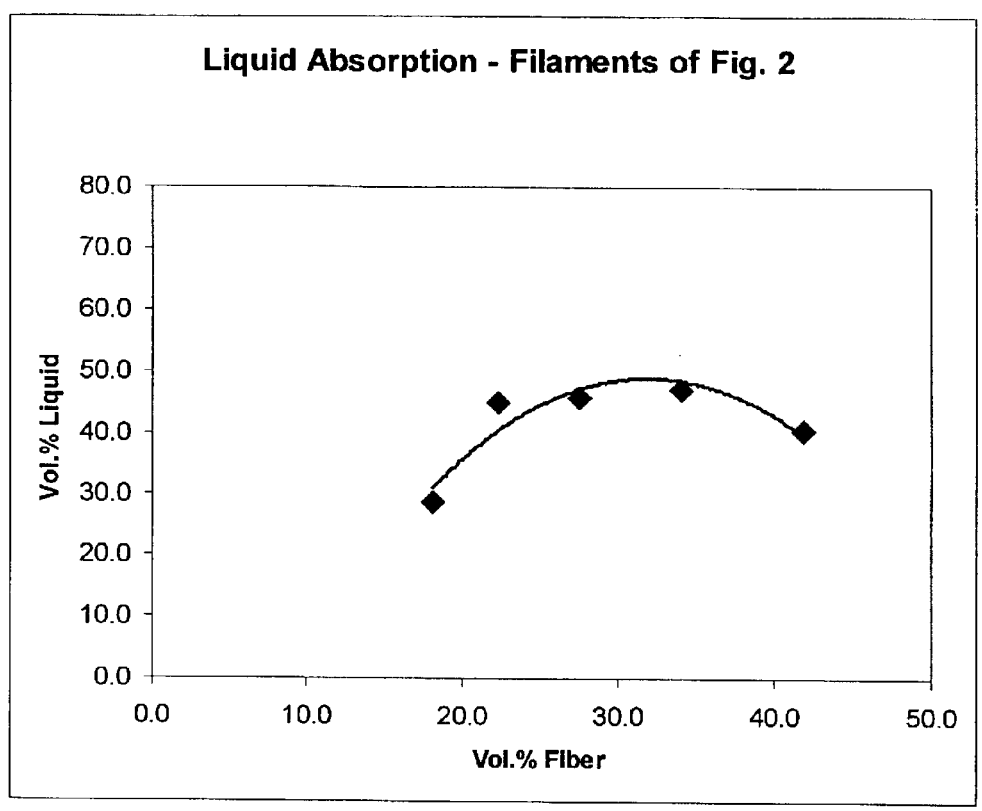
FIG. 9 shows a plot of liquid absorption vs. volume percent fiber for filaments having the cross-section illustrated in FIG. 2.

Filaments in a number from about 590 to about 1,400 were assembled into fibers and tested for absorbency by the method previously described yielding the data shown in FIG. 9. At the maximum in the absorption curve, 49 vol. % liquid was absorbed on 32 vol. % fiber corresponding to absorption of only 1.53 volumes of liquid per volume of fiber.

EXAMPLE 2

Figure 3:
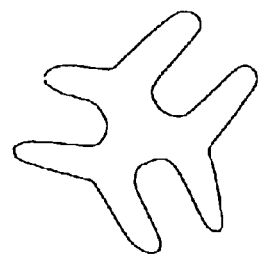
FIG. 3 shows a cross-section of a filament of a fiber of this invention showing three axes of symmetry.

A blend of 99 wt. % nylon 6 of formic acid viscosity (FAV) of 55, Grade MBM from Honeywell International Inc. and 1 wt. % acrylic acid modified polypropylene (POLYBOND® 1001) was fed into a capillary rheometer. The polymer was melted and extruded at 255° C. at the rate of about 4.8 g/min through a one-hole spinneret. The melt filament was cooled, solidified and taken up on a winder at 549 meters/min. The filament had the cross-sectional shape shown in FIG. 3.

Analysis of the filament cross-section yielded the following measurements where the terms are as previously defined:

$$A_f/A_{fp} = 0.465 \quad \Psi = 0.18 \quad d = 63.9$$

These measurements satisfy the conditions expressed by Equations 1, 2 and 3. Moreover, it is found that:

$$1.75\Psi - 0.83\, A_f/A_{fp} - 0.017\, d + 1.48 = 0.33$$

This satisfies the condition expressed by Equation 4.

Figure 10:
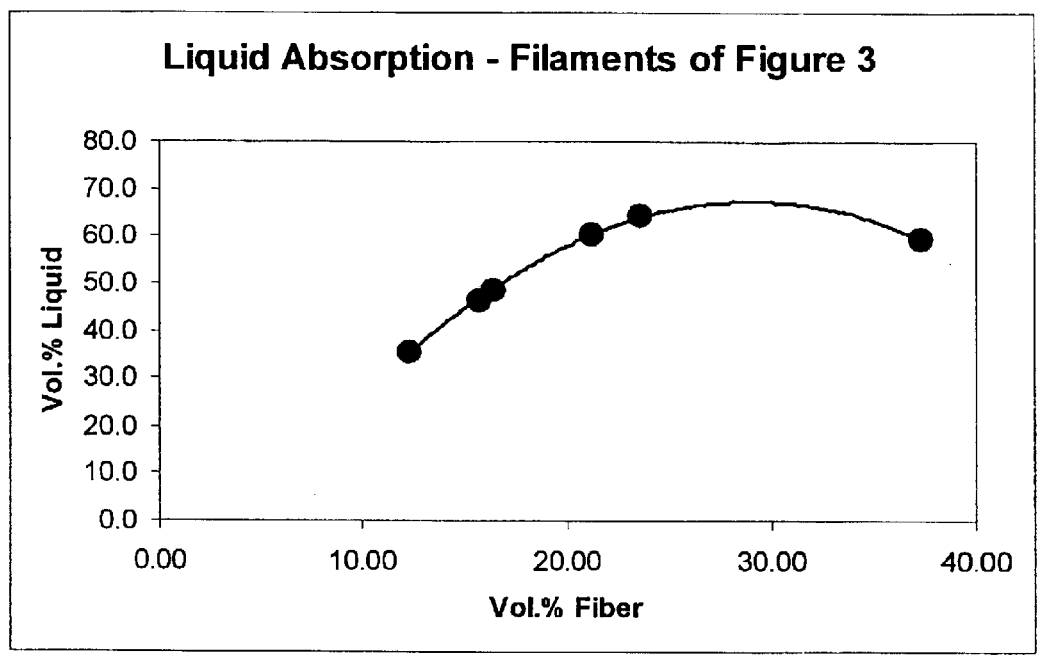
FIG. 10 shows a plot of liquid absorption vs. volume percent fiber for filaments having the cross-section illustrated in FIG. 3.

Filaments in a number from about 520 to about 1250 were assembled into fibers and liquid absorption measurements were made by the method previously described yielding the data shown in FIG. 10. At the maximum in the absorption curve, 69 vol. % liquid was absorbed on 27 vol. % fiber corresponding to absorption of 2.31 volumes of liquid per volume of fiber.

EXAMPLE 3

Figure 4:
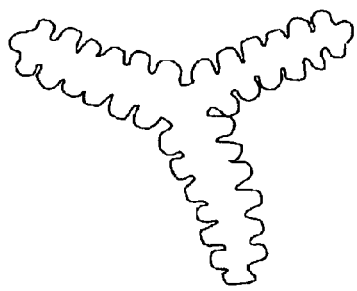
FIG. 4 shows a cross-section of a corrugated tri-lobal filament of a fiber of this invention.

A blend of 97 wt. % nylon 6 of formic acid viscosity (FAV) of 55, Grade MBM from Honeywell International Inc. and 3 wt. % acrylic acid modified polypropylene (POLYBOND®1001) was fed into a capillary rheometer. The polymer was melted and extruded at 255° C. at the rate of about 1.5 g/min through a one-hole spinneret. The melt filament was cooled, solidified and taken up on a winder at 549 meters/min. The filament had the cross-sectional shape shown in FIG. 4.

Analysis of the filament cross-section yielded the following measurements where the terms are as previously defined:

$$A_f/A_{fp} = 0.488 \quad \Psi = 0.13 \quad d = 24.9$$

These measurements satisfy the conditions expressed by Equations 1, 2 and 3. Moreover, it is found that:

$$1.75\Psi - 0.83\, A_f/A_{fp} - 0.017\, d + 1.48 = 0.87$$

This satisfies the condition expressed by Equation 4.

Figure 11:
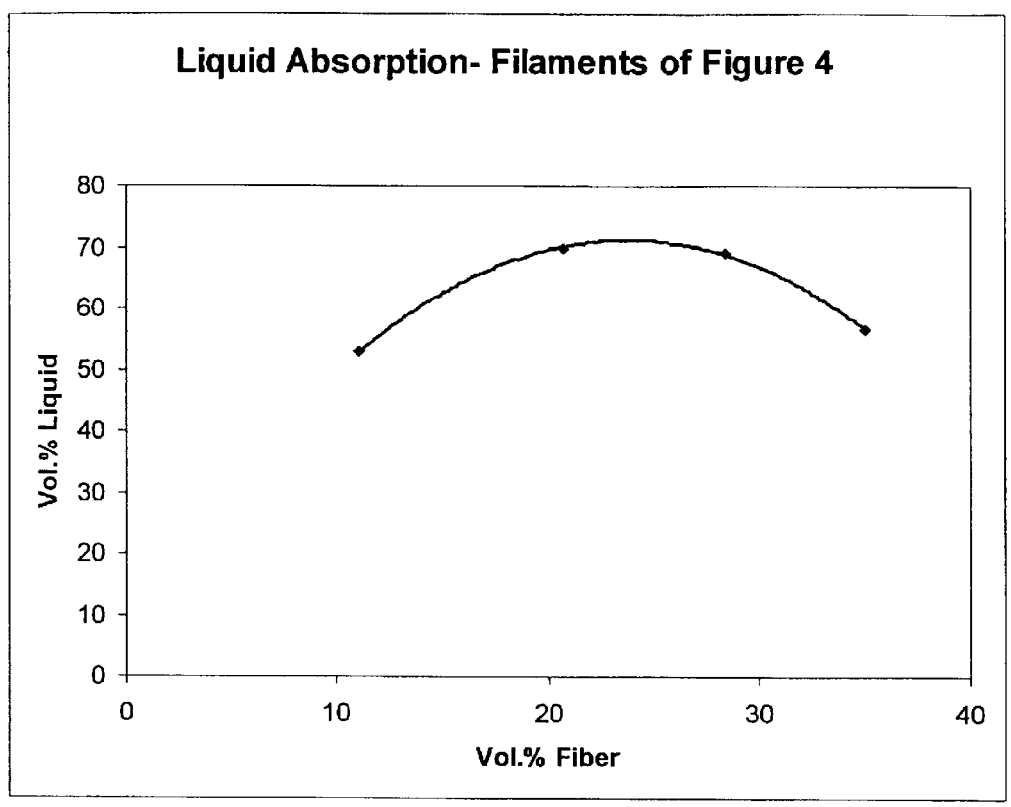
FIG. 11 shows a plot of liquid absorption vs. volume percent fiber for filaments having the cross-section illustrated in FIG. 4.

Filaments in a number from about 360 to about 1,200 were assembled into fibers and liquid absorption measurements were made by the method previously described yielding the data shown in FIG. 11. At the maximum in the absorption curve, 71.5 vol. % liquid was absorbed on 24 vol. % fiber corresponding to absorption of 2.98 volumes of liquid per volume of fiber.

EXAMPLE 4

Figure 5:
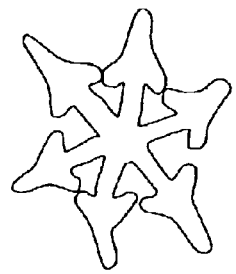
FIG. 5 shows a cross-section of a hexa-lobal filament of a fiber of this invention.

A blend of 97 wt. % nylon 6 of formic acid viscosity (FAV) of 55, Grade MBM from Honeywell International Inc. and 3 wt. % acrylic acid modified polypropylene (POLYBOND® 1001) was fed into a capillary rheometer. The polymer was melted and extruded at 245° C. at the rate of about 1.5 g/min through a one-hole spinneret. The melt filament was cooled, solidified and taken up on a winder at 549 meters/min. The filament had the cross-sectional shape shown in FIG. 5.

Analysis of the filament cross-section yielded the following measurements where the terms are as previously defined:

$$A_f/A_{fp} = 0.412 \quad \Psi = 0.20 \quad d = 21.8$$

These measurements satisfy the conditions expressed by Equations 1, 2 and 3. Moreover, it is found that:

$$1.75\Psi - 0.83\, A_f/A_{fp} - 0.017\, d + 1.48 = 1.12$$

This satisfies the condition expressed by Equation 4.

Figure 12:
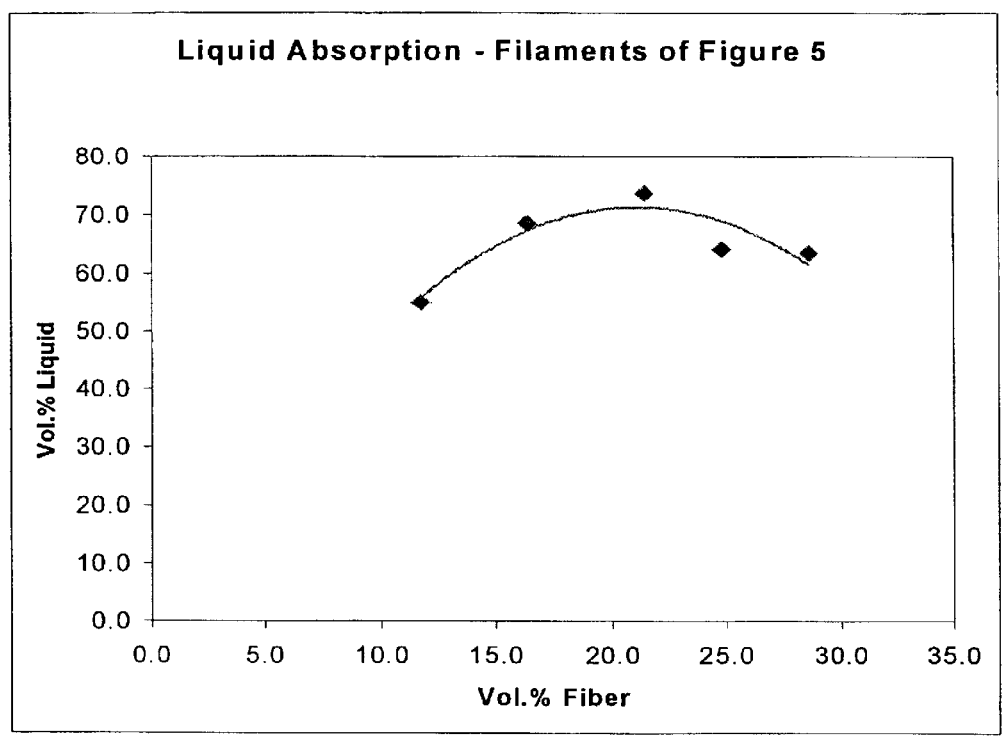
FIG. 12 shows a plot of liquid absorption vs. volume percent fiber for filaments having the cross-section illustrated in FIG. 5.

Filaments in a number from about 380 to about 950 were assembled into fibers and liquid absorption measurements were made by the method previously described yielding the data shown in FIG. 12. At the maximum in the absorption curve, 71.5 vol. % liquid was absorbed on 21.5 vol. % fiber corresponding to absorption of 3.33 volumes of liquid per volume of fiber.

EXAMPLE 5

A blend of 97 wt. % nylon 6 of formic acid viscosity (FAV) of 55, Grade MBM from Honeywell International Inc. and 3 wt. % acrylic acid modified polypropylene (POLYBOND® 1001) was fed into a capillary rheometer. The polymer was melted and extruded at 255° C. at the rate of about 1.5 g/min through a on e-hole spinneret. The melt filament was cooled, solidified and taken up on a winder at 549 meters/min. The filament had the cross-sectional shape shown in FIG. 6.

Analysis of the filament cross-section yielded the following measurements where the terms are as previously defined:

$A_f/A_{fp}=0.419 \ \Psi=0.420 \ d=20.5$

These measurements satisfy the conditions expressed by Equations 1, 2 and 3. Moreover, it is found that:

$1.75\Psi-0.83 \ A_f/A_{fp}-0.017 \ d+1.48=1.53$

This satisfies the condition expressed by Equation 4.

Figure 13:
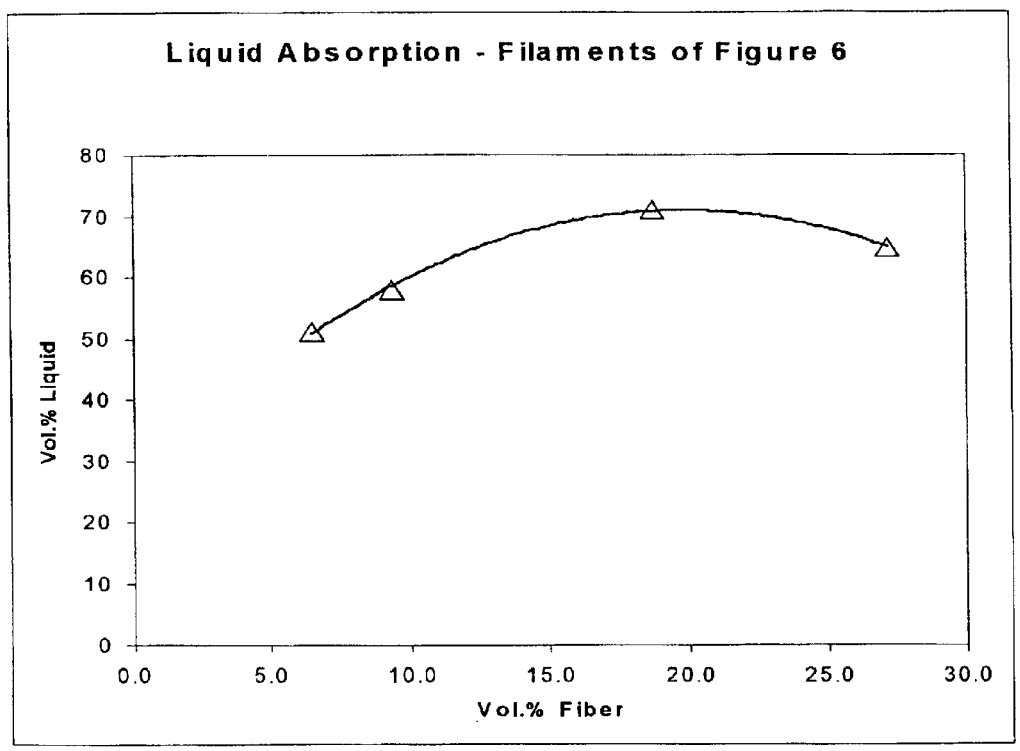
FIG. 13 shows a plot of liquid absorption vs. volume percent fiber for filaments having the cross-section illustrated in FIG. 6.
Figure 14:
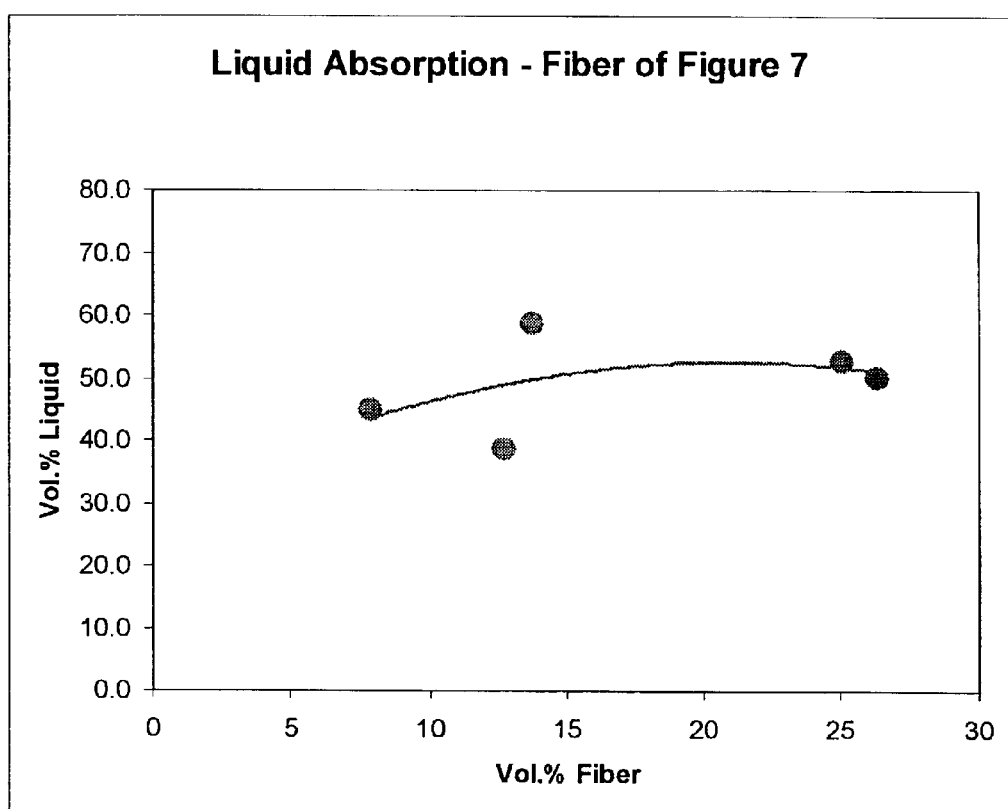
FIG. 14 shows a plot of liquid absorption vs. volume percent fiber for filaments having the cross-section illustrated in FIG. 7.

Filaments in a number from about 210 to 900 were assembled into fibers and liquid absorption measurements were made by the method previously described yielding the data shown in FIG. 13. At the maximum in the absorption curve, 71 vol. % liquid was absorbed on 20 vol. % fiber corresponding to absorption of 3.55 volumes of liquid per volume of fiber.

EXAMPLE 6

Figure 7:
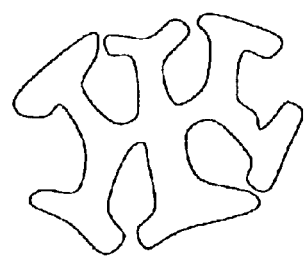
FIG. 7 shows a cross-section of a six-arm filament of a fiber of this invention.

Polyethylene terephthalate of 0.95 intrinsic viscosity (measured in a 60/40 (w/w) mixture of phenol/tetrachloroethane at 25° C.) was fed into a single screw extruder fitted with a Slack & Parr gear metering pump. The polymer was melted and extruded at 282° C. at the rate of about 0.5 g/min through a one-hole spinneret. The melt filament was cooled, solidified and taken up on a winder at 1,116 meters/min. The filament had the cross-sectional shape shown in FIG. 7.

Analysis of the filament cross-section yielded the following measurements where the terms are as previously defined:

$A_f/A_{fp}=0.480 \ \Psi=0.39 \ d=3.84$

These measurements satisfy the conditions expressed by Equations 1, 2 and 3. Moreover, it is found that:

$1.75\Psi-0.83 \ A_f/A_{fp}-0.017 \ d+1.48=1.70$

This satisfies the condition expressed by Equation 4.

Filaments in a number form about 4,800 to about 10,000 were assembled into fibers and liquid absorption measurements were made by the method previously described yielding the data shown in FIG. 11. At the maximum in the absorption curve, 52.5 vol. % liquid was absorbed on 21 vol. % fiber corresponding to absorption of 2.50 volumes of liquid per volume of fiber.

EXAMPLE 7

Figure 6:
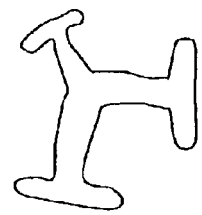
FIG. 6 shows a cross-section of a non-symmetric triad filament of a fiber of this invention.

A polyethylene terephthalate polymer of 0.95 intrinsic viscosity (measured in a 60/40 (w/w) mixture of phenol/tetrachloroethane at 25° C.) was spun into fibers having filaments whose cross-sections were of circular shape and into fibers having filaments whose cross-sections were the asymmetrical triad shape illustrated in FIG. 6. Both sets of fibers were of 3 denier per filament. The filaments of circular cross-sections failed to meet the requirements of Equations 1, 2 or 4 above and had a liquid absorption capacity less than 2 volumes of liquid per volume of fiber. The filaments whose cross-sections were as illustrated in FIG. 6 met each of the requirements of Equations 1–4 and had a liquid absorption capacity of 2.8 volumes of liquid per volume of fiber.

Non-woven fabrics were formed from each fiber using the point bonding method with points of 2 mm diameter spaced 6.4 mm apart in a square pattern. Each of the non-woven fabrics had an areal density of 550 grams per square meter. Patches, 50 mm×50 mm, were cut from each fabric, weighed, and immersed in distilled water for 10 seconds. After removal from the water, the patches were suspended by one corner for 10 seconds to drip excess liquid and then re-weighed. The saturated patches were placed between absorbent tissues. A 200 gram weight was applied to squeeze the fabrics for 5 seconds, and the patches were weighed again. The wet or dry sensation when touching the fabric was recorded.

The results of the observations were as follows:

| Filament Cross-Section | Dry Weight, g | Wet Weight, g | Squeezed Weight, g | Feel |
| --- | --- | --- | --- | --- |
| Round | 0.271 | 0.890 | 0.339 | Wet |
| FIG. 6 | 0.275 | 1.595 | 0.525 | Dry |

It is seen that the fabric consisting of fibers of the invention absorbed more liquid, retained more liquid after squeezing and felt dry to the hand even when containing 0.91 grams of liquid per gram of fiber.

Having thus described the invention in rather full detail, it will be understood that such detail need not be strictly adhered to but that further changes and modifications may suggest themselves to one skilled in the art, all falling within the scope of the invention as defined by the subjoined claims.

What is claimed is:

1. A fiber having improved liquid absorption capacity comprising: a plurality of filaments having one or more capillary channels, each capillary channel formed by capillary channel walls and a channel opening dimension, each said filament satisfying the following equations $0.1 \leq A_f/A_{fp} \leq 0.8$ $0.1 \leq \Psi \leq 1$ $1 \leq d \leq 80$ $1.75\Psi-0.83 \ A_f/A_{fp}-0.017 \ d+1.48 \geq 0$ wherein $A_f$ is the cross-sectional area occupied by the material comprising said filament;

$A_{fp}$ is the footprint area of said filament cross-section;

d is the denier of said filament;

$\Psi$ is the ratio of the square root of the sum of the cross-sectional areas of the channels in a filament to the sum of the channel opening dimensions as expressed by following equation;

$$\Psi = \frac{\sqrt{\sum_{i=1}^{N} Ac(i)}}{\sum_{i=1}^{N} L(i)}$$

wherein $Ac(i)$ is the cross-sectional area of the $i^{th}$ channel;

$L(i)$ is the dimension of the opening of the $i^{th}$ channel;

N is the number of channels; and wherein said fiber has a liquid absorption capacity of at least about two volumes of liquid per volume of fiber.

2. A fiber as recited by claim 1 wherein said fiber has a liquid absorption capacity of at least 2.5 volumes of liquid per volume of fiber.

3. A fiber as recited by claim 1 wherein said fiber has a liquid absorption capacity of at least three volumes of liquid per volume of fiber.

4. A fiber as recited by claim 1 wherein said fiber has a liquid absorption capacity of at least 3.5 volumes of liquid per volume of fiber.

5. A fiber as recited by claim 1 wherein said filaments satisfy the following equation $$1.75\Psi - 0.83\, A_f/A_{fp} - 0.017\, d + 0.98 \geq 0$$

6. A fiber as recited by claim 1 wherein said filaments satisfy the following equation $$1.75\Psi - 0.83\, A_f/A_{fp} - 0.017\, d + 0.48 \geq 0$$

7. A fiber as recited by claim 1 wherein said filaments satisfy the following equation $$1.75\Psi - 0.83\, A_f/A_{fp} - 0.017\, d \geq 0$$

8. A fiber as recited by claim 1 wherein the ratio of the cross-sectional area occupied by the material comprising said filament in proportion to the footprint area of said filament cross-section ($A_f/A_{fp}$) is from about 0.2 to about 0.6.

9. A fiber as recited by claim 1 wherein the ratio of the square root of the sum of the cross-sectional areas of the channels in a filament to the sum of the channel opening dimensions ($\Psi$) is from about 0.2 to about 0.8.

10. A fiber as recited by claim 1 wherein said filament denier is from about 3 to about 50.

11. A fiber as recited by claim 1 wherein said filament denier is from about 11 to about 50.

12. A fiber as recited by claim 1 wherein said filament denier is from about 11 to about 30.

13. A fiber as recited by claim 1 comprised of from about 10 to about 10,000 filaments.

14. A fiber as recited by claim 1 comprised of from about 50 to about 2,000 filaments.

15. A fiber as recited by claim 1 wherein the material comprising the filaments is selected from the group consisting of polyamides, polyesters, polyolefins, polyacrylics, polyalcohols, polyethers, polyketones, polycarbonates, polysulfides, polyurethanes, cellulosics and polyvinyl derivatives.

16. A fiber as recited by claim 1 wherein the material comprising the filaments is selected from the group consisting of polyamides, polyesters and polyolefins.

17. A fiber as recited by claim 1 wherein the material comprising the filaments is selected from the group consisting of nylon 6, nylon 66, polyethylene terephthalate, polytrimethylene terephthalate and polypropylene.

18. A fiber as recited by claim 16 wherein the material comprising the filaments is additionally comprised of a minor portion of hydrophilic polymer.

19. A fiber as recited by claim 16 wherein the material comprising the filaments is additionally comprised of an acrylic acid modified polypropylene.

20. A fiber having improved liquid absorption capabilities comprising: about 50 to about 2,000 filaments selected from the group consisting of nylon 6 and polyethylene terephthalate; each said filament having one or more lengthwise capillary channels, formed by a capillary channel walls, and an channel opening dimension; each said filament satisfying the following equations $$0.2 \leq A_f/A_{fp} \leq 0.6$$

$$0.2 \leq \Psi \leq 0.8$$

$$11 \leq d \leq 50$$

$$2.75\Psi - 0.83\, A_f/A_{fp} - 0.017\, d + 0.48 \geq 0$$

wherein $A_f$ is the cross-sectional area occupied by the material comprising said filament;

$A_{fp}$ is the footprint area of said filament cross-section;

d is the denier of said filament;

$\Psi$ is the ratio of the square root of the sum of the cross-sectional areas of the channels in a filament to the sum of the channel opening dimensions as expressed by following equation;

$$\Psi = \frac{\sqrt{\sum_{i=1}^{N} Ac(i)}}{\sum_{i=1}^{N} L(i)}$$

wherein

Ac(i) is the cross-sectional area of the $i^{th}$ channel;

L(i) is the dimension of the opening of the $i^{th}$ channel; and

N is the number of channels; and wherein said fiber has a liquid absorption capacity of at least about three volumes of liquid per volume of fiber.

21. A fiber comprised of multiple filaments having a cross-section illustrated in any of FIG. 1 or FIGS. 3 to 7.

22. An absorbent article comprising fibers described in of any of claims 1–21.

23. The absorbent article of claim 22 selected from the group consisting of diapers, incontinent briefs, feminine hygiene napkins, tampons, surgical sponges, wound dressings and towels.

24. The absorbent article of claim 22 selected from the group consisting of flotation booms suitable for the containment and collection of oil from the surface of water, and filters for the collection of oil from aqueous liquids.

* * * * *